United States Patent
Fouda et al.

(10) Patent No.: US 10,502,044 B2
(45) Date of Patent: Dec. 10, 2019

(54) MULTISTAGE PROCESSING AND INVERSION OF CORROSION DETECTION TOOLS

(71) Applicant: Halliburton Energy Services, Inc., Houston, TX (US)

(72) Inventors: Ahmed Elsayed Fouda, Houston, TX (US); Baris Guner, Houston, TX (US); Luis Emilio San Martin, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/570,549

(22) PCT Filed: Aug. 12, 2016

(86) PCT No.: PCT/US2016/046836
§ 371 (c)(1),
(2) Date: Oct. 30, 2017

(87) PCT Pub. No.: WO2018/031038
PCT Pub. Date: Feb. 15, 2018

(65) Prior Publication Data
US 2019/0078430 A1 Mar. 14, 2019

(51) Int. Cl.
*E21B 47/00* (2012.01)
*E21B 47/10* (2012.01)
(Continued)

(52) U.S. Cl.
CPC .......... *E21B 47/0002* (2013.01); *E21B 47/00* (2013.01); *E21B 47/08* (2013.01);
(Continued)

(58) Field of Classification Search
CPC ...... E21B 47/0002; E21B 47/08; E21B 47/10; E21B 47/102; E21B 47/00; G01V 3/18; G01V 13/00
(Continued)

(56) References Cited

U.S. PATENT DOCUMENTS

| 4,878,180 A | 10/1989 | Mcwhirter et al. |
| 9,008,970 B2 | 4/2015 | Donderici et al. |

(Continued)

FOREIGN PATENT DOCUMENTS

| WO | 2014109754 | 7/2014 |
| WO | 2015023386 | 2/2015 |

(Continued)

OTHER PUBLICATIONS

International Search Report and Written Opinion for Application No. PCT/US2016/046836 dated May 12, 2017.

*Primary Examiner* — Marrit Eyassu
(74) *Attorney, Agent, or Firm* — Benjamin Fite; C. Tumey Law Group PLLC

(57) ABSTRACT

Systems and methods for detection of downhole tubulars. A method may include disposing a corrosion detection tool in a plurality of concentric pipes, wherein the corrosion detection tool comprises a transmitter and a plurality of receivers; measuring a signal to provide a measured response; calibrating a log, wherein the calibrating comprises matching a nominal value of the measured response to a synthetic response to provide calibrated measurements; running a first inversion, wherein the first inversion comprises a first subset of the calibrated measurements that are used to compute a first estimate of properties of each of the concentric pipes; identifying pipes with an estimated thickness change from a nominal thickness to provide identified concentric pipes; selecting an innermost concentric pipe from the identified concentric pipes for computing an impulse response for deconvolution for improving vertical resolution of the measured response; applying deconvolution to a second subset of the calibrated measurements to provide calibrated and deconvolved measurements; and running a second inversion on the second subset of calibrated and deconvolved measurements, wherein the second inversion comprises at least one property of the plurality of concentric pipes.

20 Claims, 10 Drawing Sheets

US 10,502,044 B2
Page 2

(51) Int. Cl.
  *E21B 47/08* (2012.01)
  *G01V 3/18* (2006.01)
  *G01V 13/00* (2006.01)

(52) U.S. Cl.
  CPC ............ *E21B 47/10* (2013.01); *E21B 47/102* (2013.01); *G01V 3/18* (2013.01); *G01V 13/00* (2013.01)

(58) Field of Classification Search
  USPC ..................................................... 73/152.57
  See application file for complete search history.

(56) References Cited

U.S. PATENT DOCUMENTS

| | | | |
|---|---|---|---|
| 9,562,877 B2 | 2/2017 | Amineh et al. | |
| 9,562,985 B2 | 2/2017 | Donderici et al. | |
| 9,562,987 B2 | 2/2017 | Guner et al. | |
| 2009/0101337 A1* | 4/2009 | Neidhardt | E21B 47/08 166/250.01 |
| 2009/0235748 A1* | 9/2009 | Geir | G01B 17/02 73/597 |
| 2013/0193953 A1 | 8/2013 | Yarbro et al. | |
| 2015/0176401 A1* | 6/2015 | Samuel | E21B 44/00 702/6 |
| 2015/0338541 A1 | 11/2015 | Nichols et al. | |
| 2016/0245779 A1* | 8/2016 | Khalaj Amineh | E21B 47/00 |
| 2016/0290122 A1 | 10/2016 | San Martin et al. | |
| 2017/0101865 A1 | 4/2017 | Amineh et al. | |
| 2017/0115426 A1 | 4/2017 | San Martin et al. | |
| 2017/0138905 A1 | 5/2017 | Amineh et al. | |
| 2017/0176629 A1* | 6/2017 | Omeragic | G01V 3/28 |
| 2017/0285217 A1* | 10/2017 | Fang | G01V 3/38 |
| 2017/0321522 A1* | 11/2017 | Al-Hajri | E21B 43/00 |

FOREIGN PATENT DOCUMENTS

| | | |
|---|---|---|
| WO | 2015157268 | 10/2015 |
| WO | 2016007883 | 1/2016 |
| WO | 2016010915 | 1/2016 |
| WO | 201608861 | 7/2016 |
| WO | 2016108845 | 7/2016 |
| WO | 2017196357 | 11/2017 |
| WO | 2017196371 | 11/2017 |

* cited by examiner

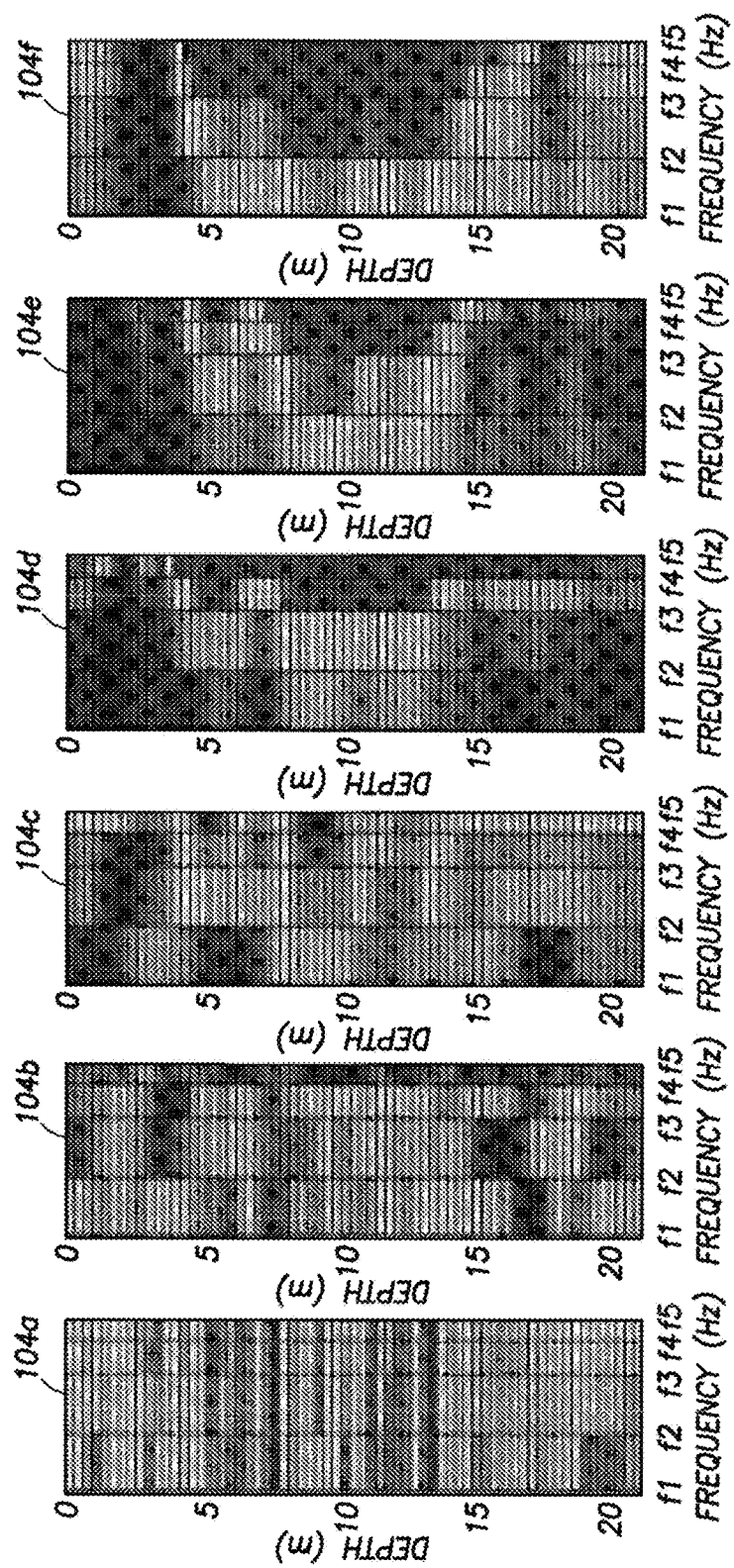

MULTISTAGE PROCESSING AND INVERSION OF CORROSION DETECTION TOOLS

BACKGROUND

For oil and gas exploration and production, a network of wells, installations and other conduits may be established by connecting sections of metal pipe together. For example, a well installation may be completed, in part, by lowering multiple sections of metal pipe (i.e., a casing string) into a borehole, and cementing the casing string in place. In some well installations, multiple casing strings are employed (e.g., a concentric multi-string arrangement) to allow for different operations related to well completion, production, or enhanced oil recovery (EOR) options.

Corrosion of metal pipes is an ongoing issue. Efforts to mitigate corrosion include use of corrosion-resistant alloys, coatings, treatments, and corrosion transfer, among others. Also, efforts to improve corrosion monitoring are ongoing. For downhole casing strings, various types of corrosion monitoring tools are available. One type of corrosion detection tool uses electromagnetic (EM) fields to estimate pipe thickness or other corrosion indicators. As an example, an EM logging tool may collect EM log data, where the EM log data may be interpreted to correlate a level of flux leakage or EM induction with corrosion. When multiple casing strings are employed together, correctly managing corrosion detection EM logging tool operations and data interpretation may be complex.

BRIEF DESCRIPTION OF THE DRAWINGS

These drawings illustrate certain aspects of some examples of the present disclosure, and should not be used to limit or define the disclosure.

FIGS. 6A and 6B are schematic illustrations of resolution-enhanced responses.

DETAILED DESCRIPTION

Figure 1:
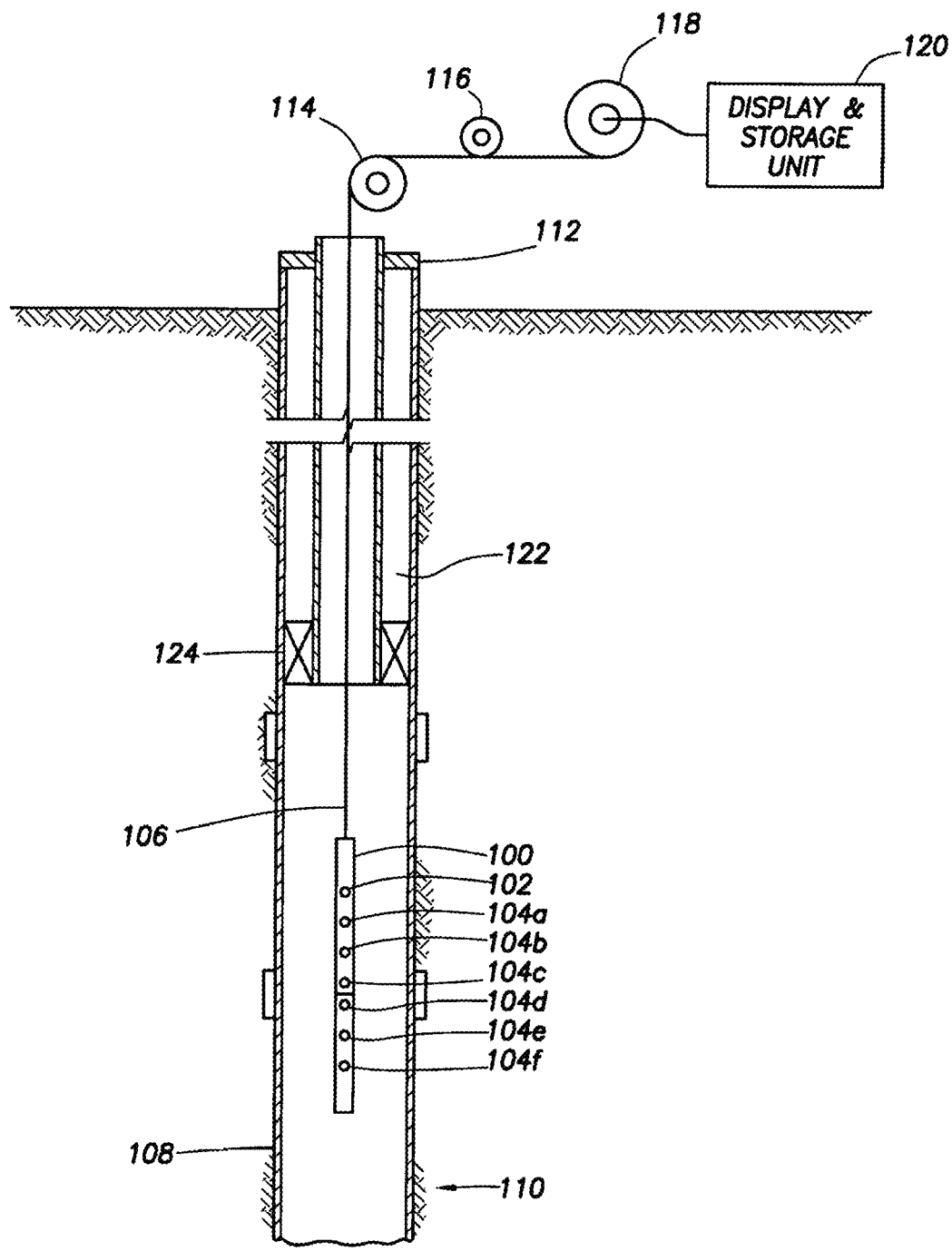
FIG. 1 is a schematic illustration of an example operating environment for a corrosion detection tool.

This disclosure may generally relate to electromagnetic pipe inspection, and, in some examples, to systems and methods for a multistage workflow for processing and inversion of data collected by corrosion detection tools. Systems and methods of the present disclosure may include applying inversion in stages where the output from the first stage may be used to determine which pipe should be selected for computing the impulse response to be used in vertical resolution enhancement deconvolution. The deconvolved responses may be used as inputs to the second inversion stage. Parameters of the pipes estimated from the first inversion stage to have small thickness changes from the nominal, are constrained in the second inversion stage to allow for more accurate thickness estimations of other pipes.

Without limitation, the processing and inversion may produce a log of the thickness of each pipe from voltage logs recorded at different receivers and different frequencies. From the thickness log, defected sections in each pipe, the size of the defect, and the amount of metal loss may be estimated. The multistage workflow may comprise running a first inversion in which a first subset of calibrated measurements may be used to compute a first estimate of the properties (diameter, thickness, and possibly magnetic permeability and electrical conductivity) of each pipe. Based on the result of the first inversion, proper deconvolution may be applied to the measurements to remove the ghost effect (also known as double indication of features) and also to improve the vertical resolution of the measurements. After that, a second inversion may be run in which at least one of the properties of a subset of pipes, determined based on the results of the first inversion, may be constrained; and the deconvolved measurements may be used to compute the thicknesses of all the pipes. Results from the second inversion may be displayed as the final inversion results. The disclosed multistage inversion workflow may be particularly important in cases involving overlapping defects on multiple pipes.

Early detection of corrosion in well casings may ensure the integrity and the safety of the well. Certain methods for downhole corrosion detection may involve running corrosion detection tools in the production tubing. Different types of corrosion detection tools may include mechanical calipers, ultrasonic acoustic tools, cameras, electromagnetic flux leakage, and electromagnetic induction tools. Among these tools, only electromagnetic induction tools may be used to determine and differentiate corrosion in separate casings beyond that in which the tool is run. Existing electromagnetic induction corrosion detection tools may comprise at least one transmitting coil and at least one receiving coil. The transmitter may generate a primary field that may induce eddy currents inside the metallic pipes, and the receiver may record secondary fields generated by the pipes. The secondary fields may bear information about the electrical properties and metal content of the pipes and may be inverted for any corrosion or loss in metal content of the pipes. Electromagnetic induction tools may be frequency-domain (FD) tools that may operate at a discrete set of frequencies (higher frequencies to inspect inner pipes and lower frequencies to inspect outer pipes). Alternatively, EM induction tools may operate in time-domain (TD) by transmitting transient pulses and measuring the decay response versus time (earlier time corresponds to inner pipes and later time corresponds to outer pipes). These tools may be referred to as pulsed eddy current corrosion detection tools.

Regardless of the type of the corrosion detection tool, model-based inversion may be needed to estimate the physical and/or electrical properties of each pipe in the casing string from measured responses. Model-based inversion may aim at finding the optimum diameter, thickness and the relative permeability of each pipe that may minimize the misfit between measurements and synthetic data generated using a computer model that simulates the tool and the well casings. Inversion may start from an initial guess of model parameters and may iteratively refine that guess until a convergence criterion is met. Constraints may be used to verify that estimated parameters lie within their physical ranges. Regularization may be used to penalize large variations of model parameters from a nominal that is available a-priori. Optimum selection of receivers and frequencies to be used in inversion may be based on the configuration (e.g., number of pipes in the string, their nominal thickness, etc.). Prior to inversion, some processing steps may need to be applied. These may include calibration, resolution enhancement and/or log depth alignment, and filtering to improve the signal-to-noise ratio.

FIG. 1 illustrates an operating environment for a corrosion detection tool 100 as disclosed herein. Corrosion detection tool 100 may comprise transmitter 102 (e.g., coil) and receivers 104a, 104b, 104c, 104d, 104e, and 104f (e.g., coil receivers). Corrosion detection tool 100 may be operatively coupled to a conveyance line 106 (e.g., wireline, slickline, coiled tubing, pipe, or the like) which may provide mechanical suspension, as well as electrical connectivity, for corrosion detection tool 100. Conveyance line 106 and corrosion detection tool 100 may extend within casing string 108 to a desired depth within the wellbore 110. Conveyance line 106, which may include one or more electrical conductors, may exit wellhead 112, may pass around pulley 114, may engage odometer 116, and may be reeled onto winch 118, which may be employed to raise and lower the tool assembly in the wellbore 110. Signals recorded by corrosion detection tool 100 may be stored on memory and then processed by display and storage unit 120 after recovery of corrosion detection tool 100 from wellbore 110. Alternatively, signals recorded by corrosion detection tool 100 may be conducted to display and storage unit 120 by way of conveyance line 106. Display and storage unit 120 may process the signals, and the information contained therein may be displayed for an operator to observe and stored for future processing and reference. Display and storage unit 120 may also contain an apparatus for supplying control signals and power to the downhole tool assembly, wherein the downhole tool assembly comprises corrosion detection tool 100.

A typical casing string 108 may extend from wellhead 112 at or above ground level to a selected depth within a wellbore 110. Casing string 108 may comprise a plurality of joints or segments of casing, each segment being connected to the adjacent segments by a threaded collar.

FIG. 1 also illustrates a typical pipe string 122, which may be positioned inside of casing string 108 extending part of the distance down wellbore 110. Pipe string 122 may be production tubing, casing, or other pipe disposed within casing string 108. A packer 124 typically may seal the lower end of the tubing-casing annulus and may secure the lower end of the tubing string 122 to the casing. The corrosion detection tool 100 may be dimensioned so that it may be lowered into the wellbore 110 through the tubing string 122, thus avoiding the difficulty and expense associated with pulling the tubing string 122 out of the well.

In logging systems, such as, for example, logging systems utilizing the corrosion detection tool 100, a digital telemetry system may be employed, wherein an electrical circuit may be used to both supply power to the corrosion detection tool 100 and to transfer data between display and storage unit 120 and corrosion detection tool 100. A DC voltage may be provided to the corrosion detection tool 100 by a power supply located above ground level, and data may be coupled to the DC power conductor by a baseband current pulse system. Alternatively, the corrosion detection tool 100 may be powered by batteries located within the downhole tool assembly, and/or the data provided by the corrosion detection tool 100 may be stored within the downhole tool assembly, rather than transmitted to the surface during logging (corrosion detection).

Transmission of electromagnetic fields by the transmitter 102 and the recordation of signals by the receivers 104a, 104b, 104c, 104d, 104e, and 104f may be controlled by an information handling system.

Systems and methods of the present disclosure may be implemented, at least in part, with an information handling system. An information handling system may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

Alternatively, systems and methods of the present disclosure may be implemented, at least in part, with non-transitory computer-readable media. Non-transitory computer-readable media may include any instrumentality or aggregation of instrumentalities that may retain data and/or instructions for a period of time. Non-transitory computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Figure 2:
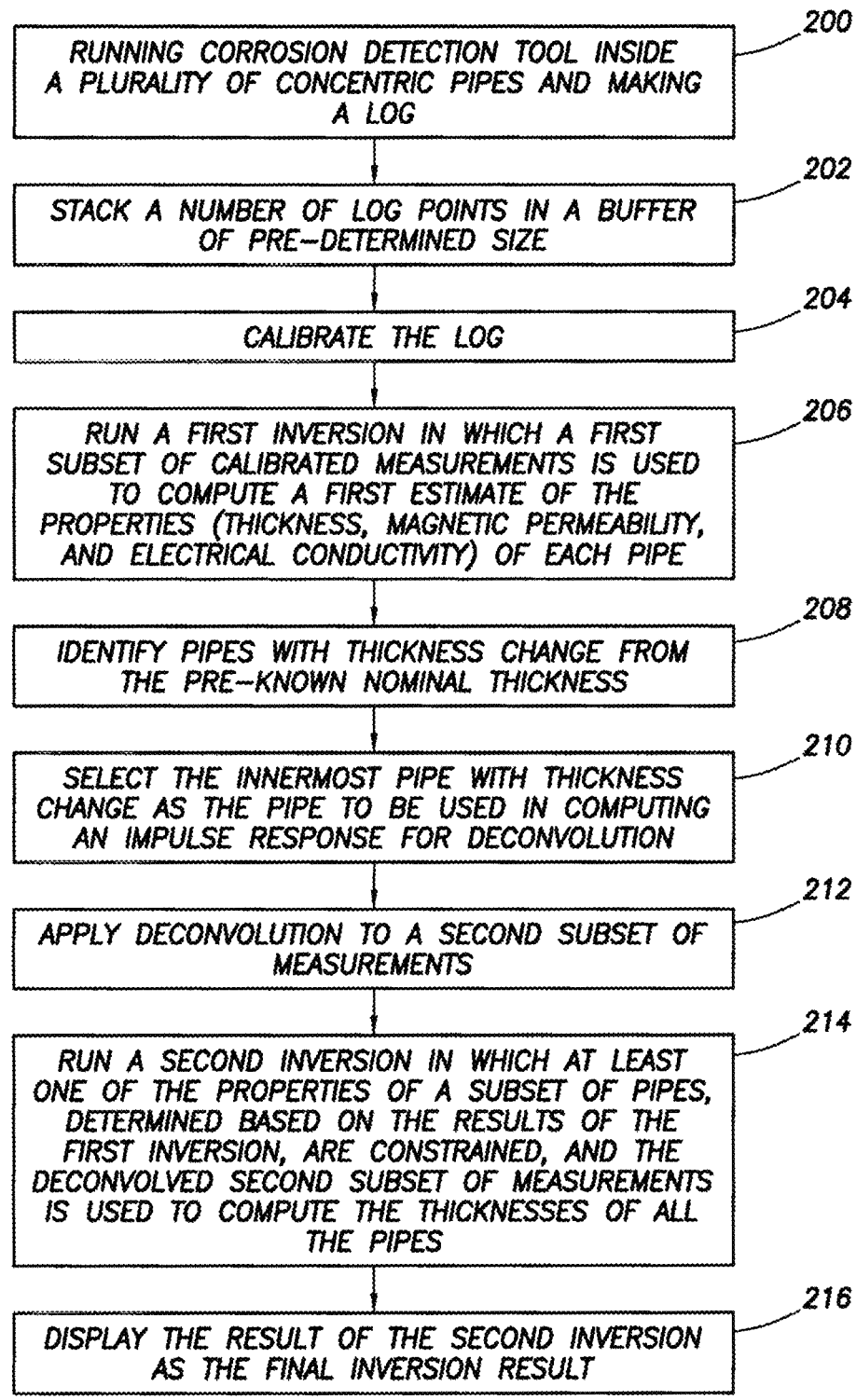
FIG. 2 is a schematic illustration of a multistage inversion workflow.

FIG. 2 schematically illustrates a workflow of the proposed multistage inversion. Box 200 provides running a corrosion detection tool 100 inside a plurality of concentric pipes and making a log. Box 202 provides stacking a number of log points in a buffer of a pre-determined size. Box 204 provides calibrating the log. Box 206 provides running a first inversion in which a first subset of calibrated measurements is used to compute a first estimate of the properties (e.g., diameter, thickness, magnetic permeability and/or electrical conductivity) of each pipe. Box 208 provides identifying pipes with thickness change from the pre-known nominal thickness. Box 210 provides selecting the innermost pipe with thickness change as the pipe to be used in computing an impulse response for deconvolution. Box 212 provides applying deconvolution to a second subset of measurements. Box 214 provides running a second inversion in which at least one of the properties of a subset of pipes, determined based on the results of the first inversion, are constrained; and the deconvolved second subset of measurements is used to compute the thickness of all the pipes. Box 216 provides displaying the result of the second inversion as the final inversion result. Additionally, the workflow may involve the following steps: 1) After the tool is run inside the cased well, log points may be stacked in an input data buffer. The buffered log may correspond to one or more casing joints. 2) When the buffer is full, the buffered log may be calibrated to compensate for any discrepancy between the real tool and the synthetic model used to invert the measurements. 3) Run a first inversion in which a first subset of the calibrated measurements may be used to compute a first estimate of the properties of each pipe. Those properties may include the diameter and thickness of the pipe, and possibly, the magnetic permeability and the electrical conductivity. The first subset preferably may include coils with small ghost effect, i.e., data from receivers relatively close to the transmitter. 4) Next, pipes with thickness change from the nominal may be identified by comparing the percentage change in estimated pipe thickness from the pre-known nominal to a pre-defined threshold; this threshold may be different for each pipe in the configuration, with inner pipes having a smaller threshold and deeper pipes having a larger threshold. For example, for the third pipe, considering the innermost as the first pipe, any section with 10% change in thickness along the log may be identified as a feature. Those features may be defects amounting to thickness loss or casing collars or other fixtures amounting to thickness gain. 5) The response of the tool to a small defect on the innermost pipe with features (identified from the previous step) may be computed using a computer model. This small defect may have any arbitrary shape with its length being as small as possible along the axial direction, but its response being measureable with sufficient accuracy with the tool. To build the synthetic model, the geometry of the pipes (number of pipes, their outer diameters, and nominal thickness) as well as their electrical and magnetic properties may need to be approximately known. For a given well, the number of pipes, their outer diameters and the nominal thicknesses are usually known a priori. The magnetic permeabilities, however, may not be precisely known and can vary significantly from one casing section to another. The average permeability and conductivity estimated from the calibration process can therefore be used in the synthetic model. 6) The response to the defect computed from the previous step may be deconvolved from the measured responses, or a subset of which, to eliminate the ghost effect and improve the resolution of the measurements. Ghost effect may be especially pronounced in long spacing receivers in frequency-domain tools. A method for improving the resolution of the logs and removing ghost effect may be based on deconvolving the impulse response of the tool from measured responses to get resolution-enhanced responses from which defects may be better visualized and interpreted. 7) After that, a second inversion may be run in which at least one of the properties of a subset of pipes, determined based on the results of the first inversion, may be constrained to be close to the determined value in the first inversion; and the deconvolved second subset of measurements may be used to compute the thicknesses of all the pipes. 8) Results of the second inversion may be taken as the final inversion result. 9) In general, the above workflow may be repeated in more than 2 stages if needed, where the inversion result from each stage may be used to constraint a subset of model parameters in the following stage.

A method for estimating the thickness of individual pipes in a multi-string pipe configuration through processing array measurements made by corrosion detection tools may comprise: 1) Making a log measurement with corrosion detection tool 100 which may comprise at least one transmitter coil (e.g., transmitter 102) and at least one receiver coil (e.g., receivers 104a, 104b, 104c, 104d, 104e, and 104f and runs inside strings of multiple nested conductive pipes. 2) Calibrating the log by matching the nominal value of the measured response to a synthetic response computed by modeling the pipes with their nominal thicknesses. 3) Running a first inversion in which a first subset of calibrated measurements may be used to compute a first estimate of the properties (e.g., thickness, and possibly magnetic permeability and electrical conductivity) of each pipe. The first subset of calibrated measurements may comprise short-spaced receivers or may comprise all receivers. Short-spaced receivers may include a distance of 30 in. (76 cm) or less. 4) Identifying pipes with estimated thickness changes from the nominal by comparing the percentage change in estimated pipe thickness from the nominal to a pre-defined threshold, which may be different for each pipe. 5) Picking the innermost pipe with thickness change as the pipe to be used in computing an impulse response for deconvolution. 6) Applying deconvolution to a second subset of measurements. The second subset of measurements may comprise long-spaced receivers or may comprise all receivers. Long-spaced receivers may include a distance of more than 30 in. (76 cm) 7) Running a second inversion in which at least one of the properties of a subset of pipes, determined based on the results of the first inversion, are constrained; and the deconvolved second subset of measurements may be used to compute the thicknesses of all the pipes. 8) Display the result of the second inversion as the final inversion result. 9) The constraint may comprise fixing the thickness of the pipes identified to have nominal thickness from the first inversion. 10) The constraint may comprise fixing the thickness of the innermost pipe in addition to the thickness of pipes identified to have nominal thickness from the first inversion. 11) The constraint may comprise fixing the thickness of the innermost pipes up to and including the innermost pipe identified to have thickness change from the first inversion. 12) The constraint may comprise fixing the magnetic permeability of the pipes in the second inversion to the values computed in the first inversion. 13) The constraint may comprise taking results of the first inversion as an initial condition for the second inversion and allowing change within a fixed range only. 14) The constraint may comprise taking results of the first inversion as an initial condition for the second inversion and allowing change, but using a large weight to heavily penalize a departure from an initial value. 15) The above workflow may be repeated in more than 2 stages if needed, where the inversion result from each stage may be used to constraint a subset of model parameters in the following stage. 16) The disclosed method may also apply to both frequency-domain and time-domain corrosion detection tools 100.

Inversion may be applied point-by-point to the log. Inversion may start from an initial guess of the model parameters (thickness and relative permeability of each pipe) and may iteratively refine model parameters to minimize the misfit between measurements and synthetic data. A parametric function (or cost function) may be formed from the linear combination of a misfit function and a stabilizing function (also known as the regularization term). The misfit function may be formed as the L2 norm of the weighted difference between observed (measured) and predicted (synthetically computed from the model) data. The stabilizing function may be formed as the L0.5, L1 or L2 norm of the weighted model parameters, and may be inclusive of a priori models and spatial functions. The model parameters may be iteratively adjusted, subject to preset constraints, to minimize the parametric functional. Constraints may be used to ensure that model parameters output from the inversion process lie within their physical ranges. In each iteration of the minimization process, convergence may be checked through pre-defined termination criteria. These criteria may include the following: (a) cost function is less than a specified tolerance; (b) change in model parameters is less than a specified tolerance; (c) change in the cost function is less than a specified tolerance; (d) Magnitude of search direction is smaller than a specified tolerance; (e) number of iterations exceeded a specified maximum.

Numerical techniques to achieve this minimization may include deterministic methods (e.g., Gauss-Newton, Trust-Region-Reflective, Levenverg-Marquardt, Steepest Descent, and Conjugate Gradients) or stochastic methods (e.g., Markov Chain Monte Carlo, Genetic Algorithms, and Simulated Annealing). In addition to a final model, the inversion may generate inversion metrics such as misfit/error, data uncertainty estimates, and model uncertainty estimates.

In gradient based minimization techniques, numerical differentiation may be used to compute the gradient (partial derivatives with respect to each one of the model parameters). Analytical differentiation may also be used if analytical expressions relating responses to model parameters are known.

The forward model may be a 1-dimensional or 2-dimensional computer model that may be evoked on-the-fly within the minimization process, or it may be a pre-computed database. If a database is used, multi-dimensional interpolation may be needed to compute the response corresponding to any given set of model parameters. In either case, the model that is used in inversion may be identical to that that may have been used in calibration.

The misfit function may be formed as the L2 norm squared of the weighted difference between calibrated measurements m and data predicted by the synthetic model s(x). The stabilizing function may be formed as the L1 norm of the weighted difference between model parameters (thickness and relative magnetic permeability of each pipe) x and the nominal model parameters, $x_0$. This way, regularization may penalize large variations of thicknesses from nominal. This may help mitigate non-uniqueness problems that may arise in cases involving large number of pipes (e.g., 4 pipes and more). The misfit function may be normalized by the number of measurements 2M to make the cost function independent of the number of measurements.

$$F_1(x) = \frac{1}{2M}\left\|W_{m,abs,1} \times \left[\text{abs}\left\{\frac{s(x)}{m}\right\} - 1\right]\right\|_2^2 + \frac{1}{2M}\left\|W_{m,angle,1} \times \text{angle}\left\{\frac{s(x)}{m}\right\}\right\|_2^2 + |W_{x,1} \times (x - x_0)|_1 \quad (1)$$

where x: is the vector of N model parameters $x = [t_1, \ldots, t_{N_p}, \ldots, d_1, \ldots, d_{N_p}, \mu_1, \mu_{N_p}, \sigma_1, \ldots, \sigma_{N_p}]$, where $N_p$ is the number of pipes, t is the thickness of the pipe, d is the inner or outer diameter of the pipe, μ is the relative magnetic permeability and σ is the electrical conductivity.

m: vector of M complex measurements at different frequencies and receivers. $M = N_{Rx} \times N_f$ where $N_{Rx}$ is the number of receivers and $N_f$ is the number of frequencies.

s(x): vector of M forward model responses $W_{m,abs,1}$, $W_{m,angle,1}$: measurement magnitude and phase weight matrices of the first inversion stage. These are M×M diagonal matrices used to assign different weights to different measurements based on the relative quality or importance of each measurement.

$W_{x,1}$: N×N diagonal matrix of regularization weights of the first inversion stage.

$x_0$: vector of nominal model parameters

And for an N-dimensional vector y, $\|y\|_2^2 = \Sigma_{i=1}^N |y_i|^2$ and $|y|_i = \Sigma_{i=1}^N |y_i|$. Also, note the division $$\frac{s(x)}{m}$$

is element-wise division.

The systems and methods in which the thickness and permeability of all pipes are solved for may be known as unrestricted inversion. Alternatively, a restricted problem may be solved where only a subset of the model parameters are assumed to be unknown while others are assumed to have pre-known values. A variant of this last case may be the case in which a subset of values may be assumed to be pre-known but changes may still be allowed but may be heavily penalized by the regularization term. In cases where a sufficiently diverse set of independent measurements (multiple receivers and multiple frequencies) is available, unrestricted inversion may yield a solution that best fits measured responses due to an increased number of degrees of freedom (model parameters). In other cases where not as many measurements are available or when the number of pipes in the string is too large (e.g., 4 pipes or more), restricted inversion may be needed to reduce the number of unknowns. Different forms of restricted inversion may include: 1) Solve for the individual thickness of each pipe, the magnetic permeability of the innermost pipe, and one magnetic permeability common to all other pipes. 2) Solve for the individual thickness of each pipe and one magnetic permeability common to all pipes. 3) Solve for the individual thickness of each pipe and correct the permeability of all pipes to the average value estimated from the calibration step.

The cost function of the 2nd inversion stage may be given by:

$$F_2(x) = \frac{1}{2M}\left\|W_{m,abs,2} \times \left[\text{abs}\left\{\frac{s(x)}{\hat{m}}\right\} - 1\right]\right\|_2^2 + \frac{1}{2M}\left\|W_{m,angle,2} \times \text{angle}\left\{\frac{s(x)}{\hat{m}}\right\}\right\|_2^2 + |W_{x,2}(x_1) \times (x - x_1)|_1$$

where $\hat{m}$ is the resolution enhanced measurements after applying deconvolution based on the outcome from the first stage.

$W_{m,abs,2}$, $W_{m,angle,2}$ are the magnitude and phase weight matrices of the second inversion stage. In general, different channels (receiver/frequency duplet) may be assigned different weights in the first and second inversion stages.

$W_{x,2}(x_1)$: is the matrix of regularization weights of the second inversion stage. Note that regularization in the second stage is a function of the inversion of the inversion results of the first stage $x_1$.

Regularization may be used to penalize (or constraint) changes of some model parameters in the second inversion stage from their values estimated in the first stage. These constraints may take any of the following forms: 1) The constraint may comprise increasing the regularization weights of the thickness of the pipes identified to have nominal thickness from the first inversion. 2) The constraint may comprise increasing the regularization weights of the thickness of the innermost pipe in addition to the thickness of pipes identified to have nominal thickness from the first inversion. 3) The constraint may comprise increasing the regularization weights of the thickness of the innermost pipes up to and including the innermost pipe identified to have a thickness change from the first inversion. In addition to any of the above, the constraint may comprise correcting the magnetic permeability of the pipes in the second inversion to the values computed in the first inversion.

In addition to, or instead of, applying constraints through the regularization term, lower and upper bounds may be defined for each model parameter. These bounds may be different in the first and second inversion stages. The inverse problem may be solved by finding the set of optimum model parameters $x_{opt}$ that may minimize the cost function, subject to constraints on the model parameters, that is $$x_{opt} = \mathrm{argmin}_x(F(x)), \; x_{lb} \leq x_{opt} \leq x_{ub} \quad (3)$$

Model parameters may be constrained to physical ranges to eliminate any non-physical results. For example, the thickness may range from zero to slightly larger than the nominal thickness to account for defects and pipe variations around the nominal in sections where no collars are expected. In other sections where collars may be expected, the thickness may range from zero to the nominal pipe thickness, plus the nominal collar thickness. The relative magnetic permeability may range from $\mu_{min}$ to $\mu_{max}$ with the limits chosen depending on the a priori knowledge of the type of steel of the pipes used. Eq. (3) describes a non-linear least square constrained optimization problem. It may be solved in many ways, including gradient-based and non-gradient-based methods.

Figure 3:
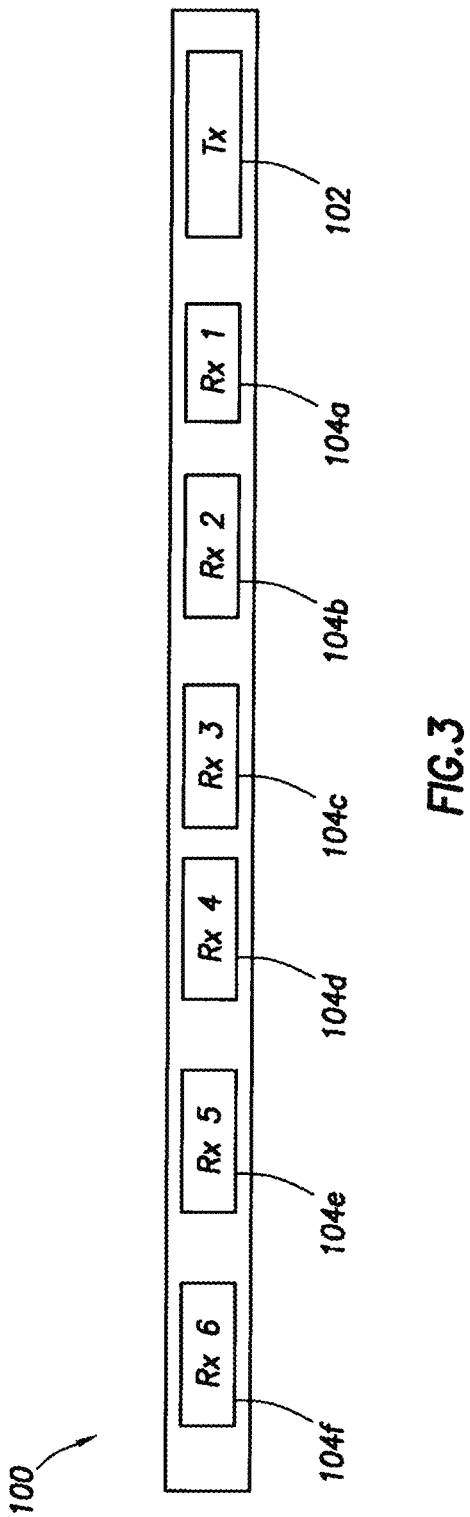
FIG. 3 is a schematic illustration of a frequency-domain corrosion detection tool with 1 transmitter and 6 receivers.

FIG. 3 is a schematic illustration of the corrosion detection tool 100. The corrosion detection tool 100 may include one transmitting coil (e.g., transmitter 102), and six receiving coils (e.g., receivers 104a, 104b, 104c, 104d, 104e, and 104f). The transmitter 102 may have a core with any suitable relative permeability, conductivity, and outer diameter. The receivers 104a, 104b, 104c, 104d, 104e, and 104f may be without a core. The corrosion detection tool 100 may be run into concentric pipes disposed in a wellbore 110 (e.g., FIG. 1) and used to obtain measurements. The concentric pipes may include 2 or more concentric pipes, including 2 concentric pipes, 3 concentric pipes, 4 concentric pipes, 5 concentric pipes, or more. The measurements may be obtained at a variety of frequencies as will be appreciated by those of ordinary skill in the art, with the benefit of this disclosure.

An illustrative example using the corrosion detection tool 100 of FIG. 3 will now be described. In this example, the transmitter 102 may have a relative permeability of about 200 H/m, conductivity of about 0.01 S/m, and OD (outer diameter) of about 0.8 in (2 cm). The receivers 104a, 104b, 104c, 104d, 104e, and 104f may be without a core. In this example, measurements may be performed at the following frequencies: $f_1$, $f_2$, $f_3$ and $f_4$, and the corrosion detection tool 100 may be run inside 5 concentric pipes. Parameters of the pipes, for this example, are summarized in Table 1. As an example, the 4th pipe has three 2-ft (0.6 m) defects while the $5^{th}$ pipe has a large, 6-ft (1.8 m) long defect and a smaller 1-ft (0.3 m) defect adjacent to it as shown in Table 1.

TABLE 1

Parameters of the pipes.

| | Pipe | | | | |
|---|---|---|---|---|---|
| | 1 | 2 | 3 | 4 | 5 |
| OD | 2.875 in (7.3 cm) | 7 in (18 cm) | 9.625 in (24.5 cm) | 13.375 in (34 cm) | 18.625 in (47.3 cm) |
| Thickness | 0.217 in (0.55 cm) | 0.324 in (0.82 cm) | 0.545 in (1.4 cm) | 0.514 in (1.3 cm) | 0.435 in (1.1 cm) |
| Relative Permeability [H/m] | 74 H/m | 74 H/m | 74 H/m | 74 H/m | 74 H/m |
| Conductivity | 4 MS/m | 4 MS/m | 4 MS/m | 4 MS/m | 4 MS/m |
| Length | 20 ft (6 m) | 20 ft (6 m) | 20 ft (6 m) | 20 ft (6 m) | 20 ft (6 m) |
| Defect(s) | None | None | None | 0.09 in × 2 ft (0.2 cm × 0.6 m), center line at 5 ft (1.5 m) (17.5%); 0.05 in × 2 ft, center line at 9 ft (2.7 m) (10%); 0.03 in × 2 ft (0.07 cm × 0.6 m), center line at 13 ft (4 m) (6%) | 0.135 in × 6 ft (0.34 cm × 1.8 m), center line at 10 ft (3 m) (31%); 0.03 in × 1 ft (0.08 cm × 0.3 m), center line at 13.5 ft (4.1 m) (7%) |

Figure 4A:
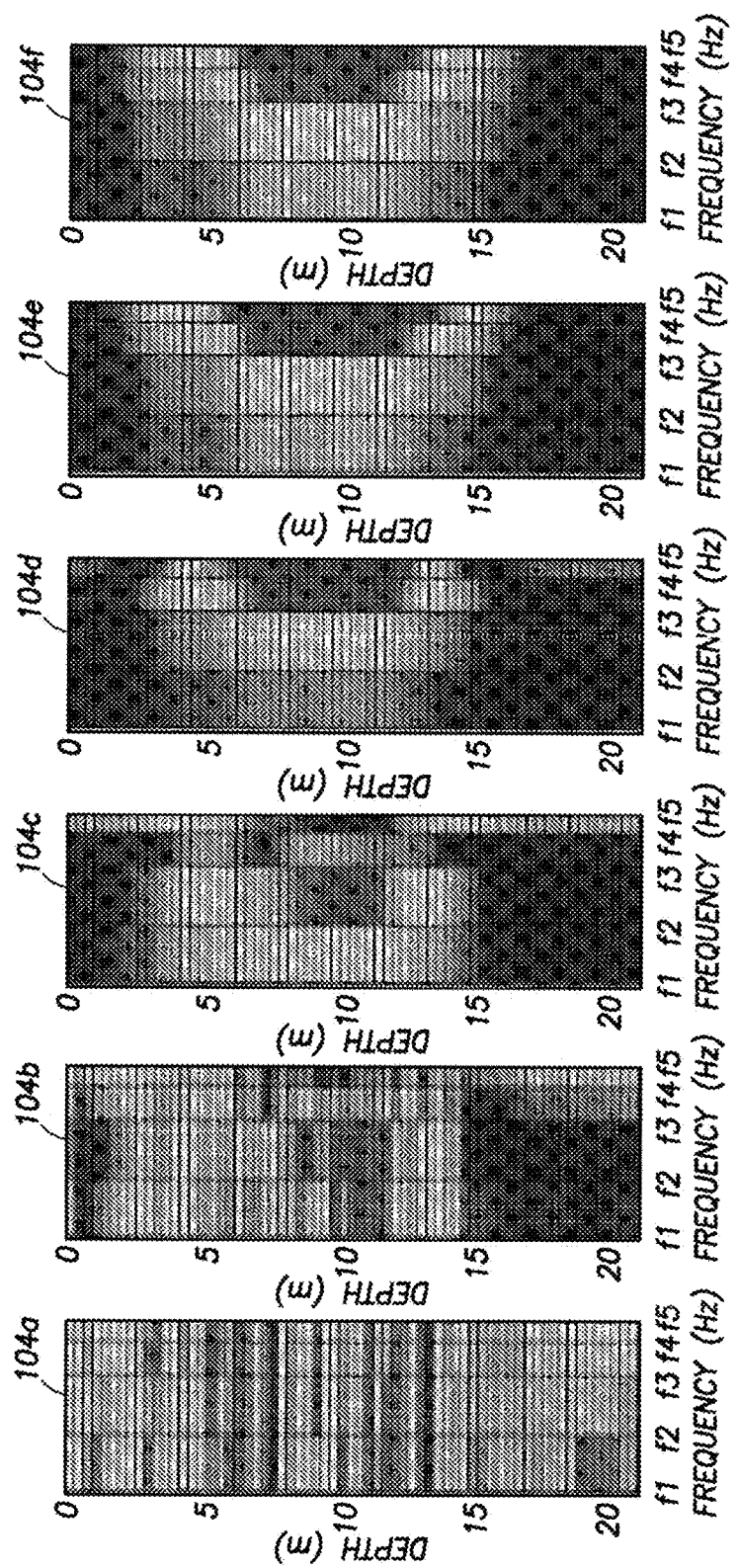
FIGS. 4A and 4B are schematic illustrations of raw responses.
Figure 4B:
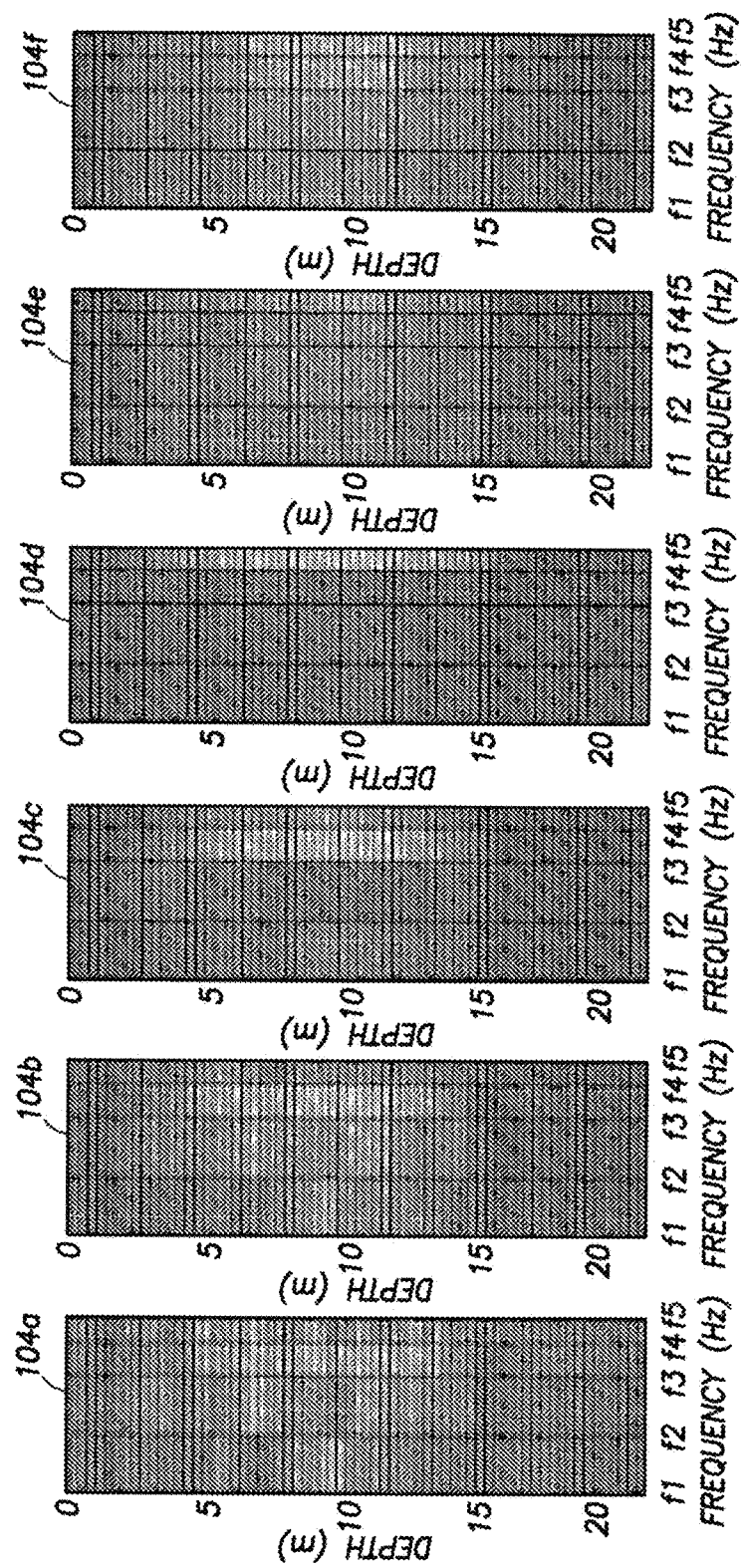

For this example, a radial 1D (R-1D) model is used in the inversion. First, raw measurements are calibrated to match the synthetic response at a nominal section of the log. Estimates of the average electrical conductivity and the average magnetic permeability of all pipes are also obtained during the calibration step. Calibrated responses for all receivers 104*a*, 104*b*, 104*c*, 104*d*, 104*e*, and 104*f* and frequencies are shown in FIGS. 4A and 4B. Each frequency/receiver log may be normalized to the point that has the minimum magnitude. FIG. 4A illustrates the raw magnitude response. FIG. 4B illustrates the raw phase response. In the first stage of the inversion, receivers 104*a*, 104*b* and 104*c* are used.

Figure 5:
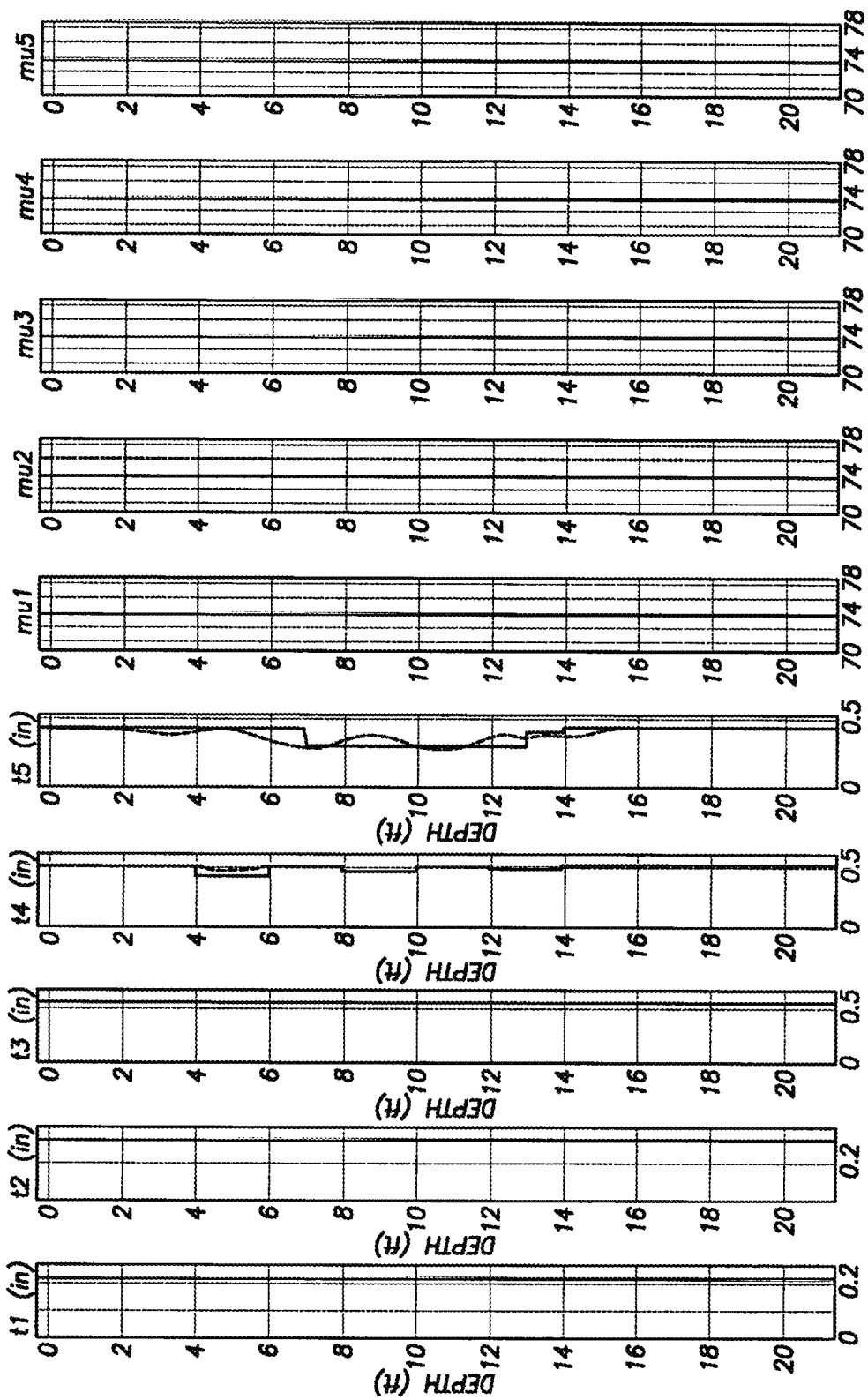
FIG. 5 is a schematic illustration of estimated pipe thickness and relative permeability from Stage 1.

The inversion results of this first stage for this example are shown in FIG. 5. In this example, the inversion is be used to solve for the thickness of each pipe, the magnetic permeability of the innermost pipe, and one magnetic permeability common to all other pipes. Inversion is used to capture the depth and thickness of the defects on the 4th and 5th pipes while estimating the thickness of non-defected inner pipes reasonably accurately. However, ghost effects due to the defects in pipe 4 are visible in the outermost pipe (at ~3 ft (0.9 m) and ~15 ft (4.5 m)). This may cause the detection of spurious defects.

Figure 6B:
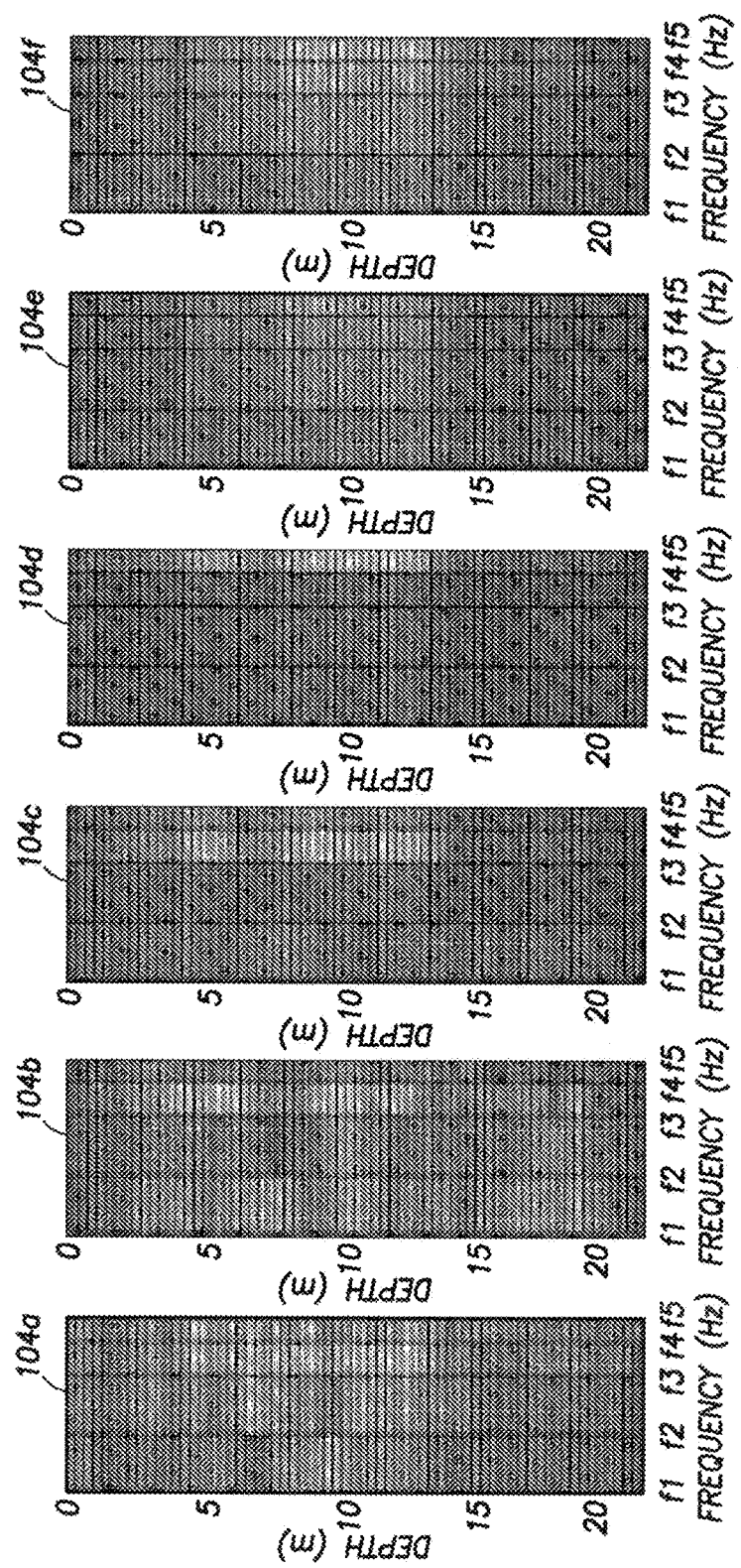

The example continues with the resolution of the responses enhanced using deconvolution in the second stage. The 4th pipe is chosen to calculate the deconvolution response since this pipe shows as the innermost pipe, in this example, with a defect in the first stage of inversion. Magnitude and phase of the resolution enhanced responses, for this example, are shown in FIGS. 6A and 6B. As illustrated by FIGS. 6A and 6B, compared with the original responses shown in FIGS. 4A and 4B, peaks of the resolution enhanced responses are better aligned with the location of the defects. Using the resolution enhanced responses of receivers 104*e* and 104*f* (e.g., shown on FIG. 3, which have longer spacings, and thus, more suited to inspect outer pipes) and correcting the thicknesses of the pipes up to and including the innermost pipe with a defect, as well as, the permeabilities of all the pipes to those obtained in stage 1, inversion for the stage 2 may be run. Thus, for this particular example, only the thickness of the 5th pipe is inverted in this stage.

Figure 7:
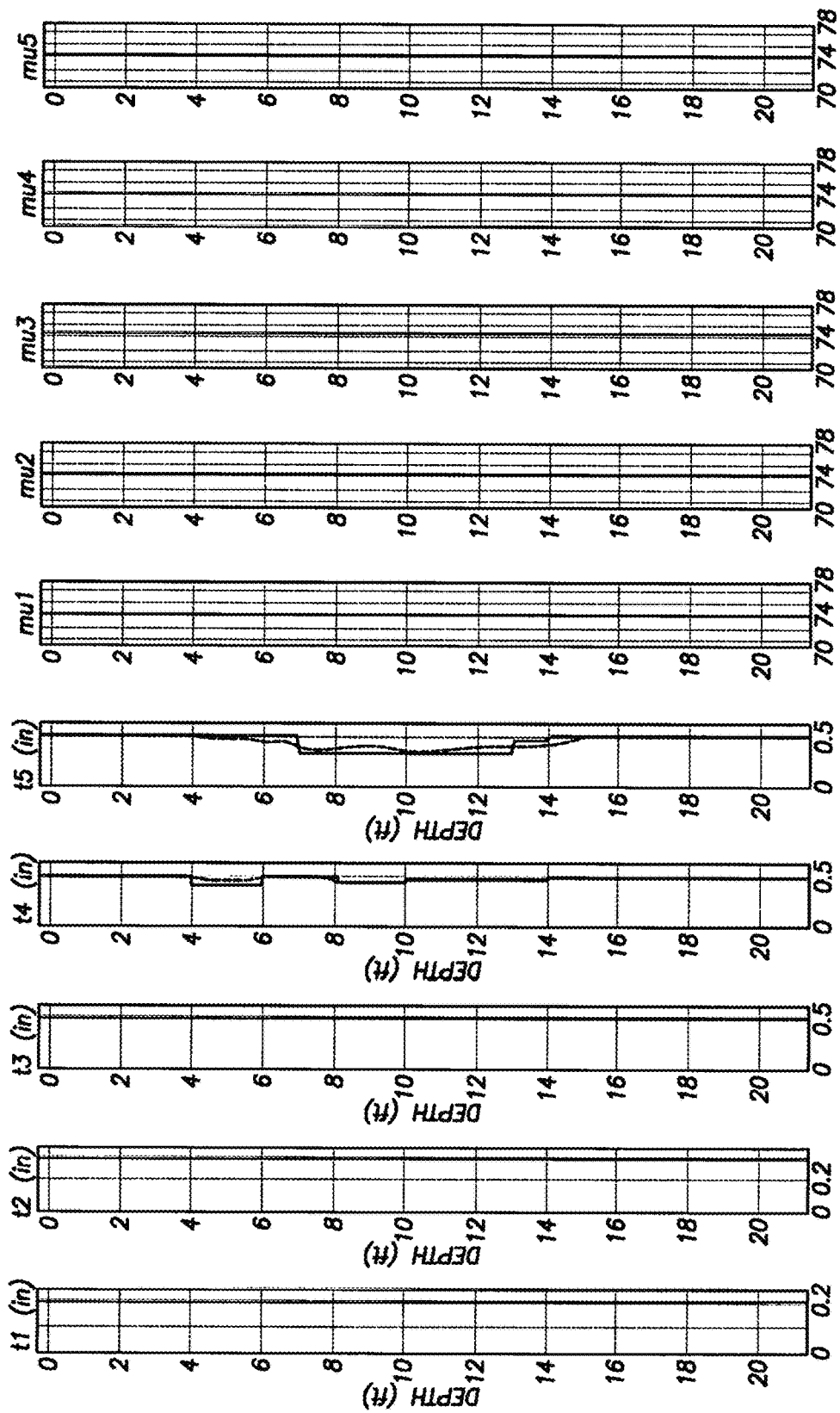
FIG. 7 is a schematic illustration of estimated pipe thickness and relative permeability from Stage 2.
Figure 8:
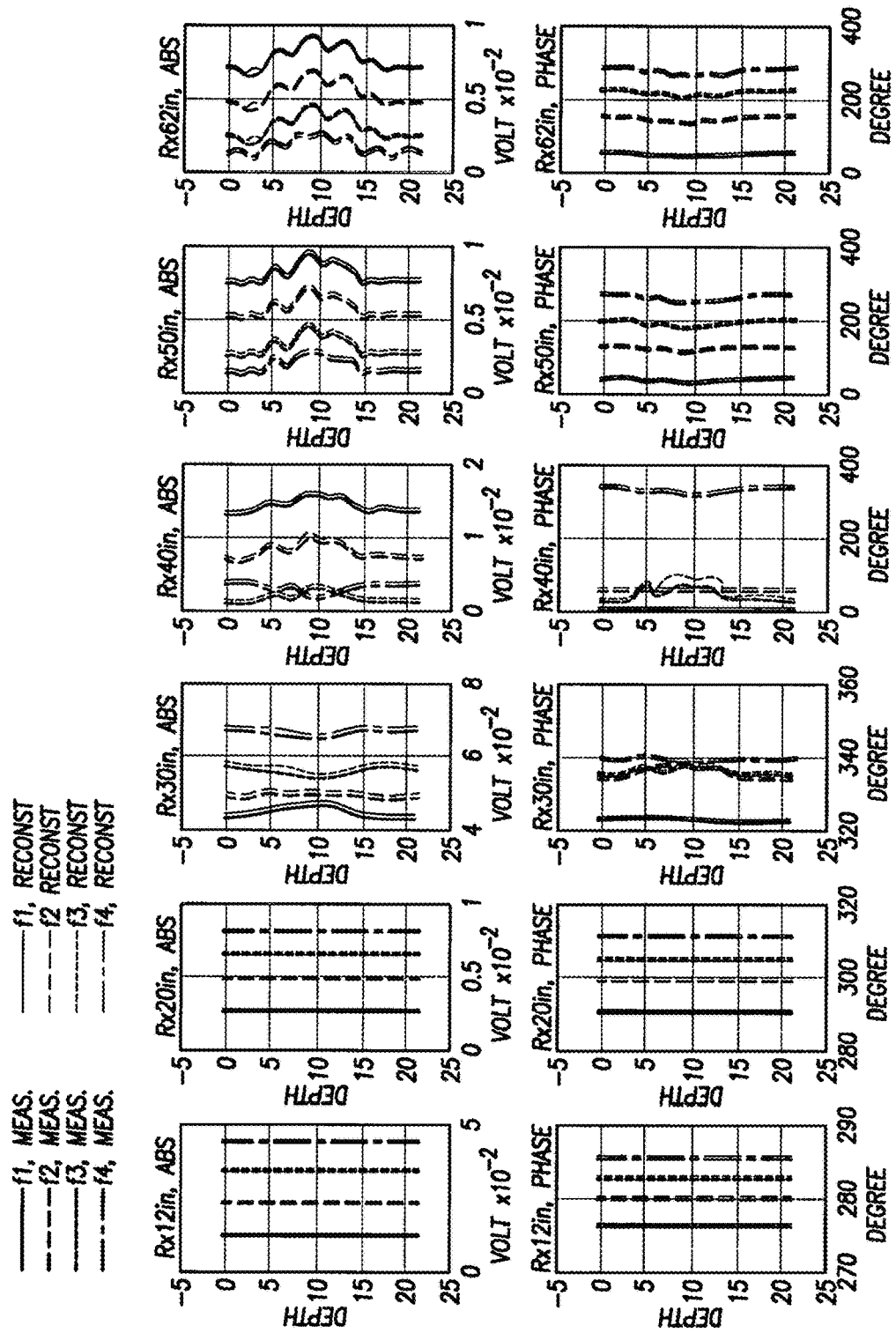
FIG. 8 is a schematic illustration of measured vs. reconstructed responses.

FIG. 7 shows the final inversion results, for this example, after the second stage. As illustrated, ghost effect is significantly reduced and thickness estimates of the defected regions on the $5^{th}$ pipe are improved. To further assess the quality of convergence, this example continues with reconstructions responses corresponding to the inverted parameters using the RID model and compared with the measured responses, as shown in FIG. 8. In general, an accurate fit is observed at all receivers 104 (e.g., receivers 104*a*, 104*b*, 104*c*, 104*d*, 104*e*, and 104*f* shown on FIG. 3).

Accordingly, this disclosure describes systems and methods that may be used for inspection of downhole tubulars. Without limitation, the systems and methods may further be characterized by one or more of the following statements:

Statement 1: A method comprising: disposing a corrosion detection tool in a plurality of concentric pipes, wherein the corrosion detection tool comprises a transmitter and a plurality of receivers; measuring a signal to provide a measured response; calibrating a log, wherein the calibrating comprises matching a nominal value of the measured response to a synthetic response to provide calibrated measurements; running a first inversion, wherein the first inversion comprises a first subset of the calibrated measurements that are used to compute a first estimate of properties of each of the concentric pipes; identifying pipes with an estimated thickness change from a nominal thickness to provide identified concentric pipes; selecting an innermost concentric pipe from the identified concentric pipes for computing an impulse response for deconvolution for improving vertical resolution of the measured response; applying deconvolution to a second subset of the calibrated measurements to provide calibrated and deconvolved measurements; and running a second inversion on the second subset of calibrated and deconvolved measurements, wherein the second inversion comprises at least one property of the plurality of concentric pipes.

Statement 2: The method of statement 1, wherein the properties of the first estimate comprise thickness, inner diameter, outer diameter, magnetic permeability, or electrical conductivity.

Statement 3: The method of statement 1 or statement 2, further comprising computing the synthetic response by modeling the concentric pipes with their nominal thicknesses.

Statement 4: The method of any of the preceding statements, wherein the first subset of the calibrated measurements comprise measurements from short-spaced receivers or measurements from all the receivers.

Statement 5: The method of any of the preceding statements, wherein the identifying comprises comparing a percentage change in estimated pipe thickness from the nominal thickness to a pre-defined threshold.

Statement 6: The method of any of the preceding statements, wherein the second subset of the calibrated measurements comprise measurements from long-spaced receivers or measurements from all the receivers.

Statement 7: The method of any of the preceding statements, wherein the at least one property of the plurality of concentric pipes is constrained.

Statement 8: The method of any of the preceding statements, wherein the at least one property of the plurality of concentric pipes is determined based on results of the first inversion.

Statement 9: The method of any of the preceding statements, further comprising displaying a result of the second inversion as a final inversion result.

Statement 10: A method comprising: disposing a corrosion detection tool in a plurality of concentric pipes, wherein the corrosion detection tool comprises a transmitter and a plurality of receivers; stacking a number of log points in a buffer; running a first inversion, wherein the first inversion comprises a first subset of calibrated measurements that are used to compute a first estimate of properties of each of the concentric pipes; identifying one or more of the concentric pipes with an estimated thickness change from a nominal thickness to provide identified concentric pipes; selecting an innermost pipe from the identified concentric pipes with a thickness change for computing an impulse response for deconvolution; applying the deconvolution to a second subset of measurements; and running a second inversion, wherein the second inversion comprises at least one property of the plurality of concentric pipes, wherein the at least one property of the plurality of concentric pipes is constrained with a constraint.

Statement 11: The method of statement 10, wherein the at least one property of the plurality of concentric pipes is determined based on results of the first inversion.

Statement 12: The method of statement 10 or statement 11, further comprising displaying a result of the second inversion as a final inversion result.

Statement 13: The method of any of statements 10 to 12, wherein the constraint comprises a thickness of the concentric pipes identified to have nominal thickness from the first inversion.

Statement 14: The method of any of statements 10 to 13, wherein the constraint comprises a thickness of an innermost concentric pipe in addition to a thickness of concentric pipes identified to have a nominal thickness from the first inversion.

Statement 15: The method of any of statements 10 to 14, wherein the constraint comprises a thickness of an innermost concentric pipe up to and including an innermost concentric pipe identified to have a thickness change from the first inversion.

Statement 16: The method of any of statements 10 to 15, wherein the at least one property of the plurality of concentric pipes of the second inversion comprises a magnetic permeability that is constrained to values computed in the first inversion.

Statement 17: The method of any of statements 10 to 16, wherein the constraint comprises results of the first inversion as an initial condition for the second inversion and an allowed thickness change within a fixed range only.

Statement 18: The method of any of statements 10 to 17, wherein the constraint further comprises a large weight to heavily penalize departure from an initial value.

Statement 19: A system comprising: a corrosion detection tool, wherein the corrosion detection tool comprises a transmitter and a plurality of receivers; and an information handling system operable to: measure a signal to provide a measured response; calibrate a log by matching a nominal value of the measured response to a synthetic response; and run a first inversion, wherein the first inversion comprises a first subset of calibrated measurements that are used to compute a first estimate of properties of one or more pipes.

Statement 20: The system of statement 19, wherein the information handling system is further operable to identify the one or more pipes with an estimated thickness change from a nominal thickness to provide identified one or more pipes.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A method comprising:
    disposing a corrosion detection tool in a plurality of concentric pipes, wherein the corrosion detection tool comprises a transmitter and a plurality of receivers;
    measuring a signal to provide a measured response;
    calibrating a log, wherein the calibrating comprises matching a nominal value of the measured response to a synthetic response to provide calibrated measurements;
    running a first inversion, wherein the first inversion comprises a first subset of the calibrated measurements that are used to compute a first estimate of properties of each of the concentric pipes;
    identifying pipes with an estimated thickness change from a nominal thickness to provide identified concentric pipes;
    selecting an innermost concentric pipe from the identified concentric pipes for computing an impulse response for deconvolution for improving vertical resolution of the measured response;
    applying deconvolution to a second subset of the calibrated measurements to provide calibrated and deconvolved measurements; and
    running a second inversion on the second subset of calibrated and deconvolved measurements, wherein the second inversion comprises at least one property of the plurality of concentric pipes.

2. The method of claim 1, wherein the properties of the first estimate comprise thickness, inner diameter, outer diameter, magnetic permeability, or electrical conductivity.

3. The method of claim 1, further comprising computing the synthetic response by modeling the concentric pipes with their nominal thicknesses.

4. The method of claim 1, wherein the first subset of the calibrated measurements comprise measurements from short-spaced receivers or measurements from all the receivers.

5. The method of claim 1, wherein the identifying comprises comparing a percentage change in estimated pipe thickness from the nominal thickness to a pre-defined threshold.

6. The method of claim 1, wherein the second subset of the calibrated measurements comprise measurements from long-spaced receivers or measurements from all the receivers.

7. The method of claim 1, wherein the at least one property of the plurality of concentric pipes is constrained.

8. The method of claim 1, wherein the at least one property of the plurality of concentric pipes is determined based on results of the first inversion.

9. The method of claim 1, further comprising displaying a result of the second inversion as a final inversion result.

10. A method comprising:
disposing a corrosion detection tool in a plurality of concentric pipes, wherein the corrosion detection tool comprises a transmitter and a plurality of receivers;
stacking a number of log points in a buffer;
running a first inversion, wherein the first inversion comprises a first subset of calibrated measurements that are used to compute a first estimate of properties of each of the concentric pipes;
identifying one or more of the concentric pipes with an estimated thickness change from a nominal thickness to provide identified concentric pipes;
selecting an innermost pipe from the identified concentric pipes with a thickness change for computing an impulse response for deconvolution;
applying the deconvolution to a second subset of measurements; and
running a second inversion, wherein the second inversion comprises at least one property of the plurality of concentric pipes, wherein the at least one property of the plurality of concentric pipes is constrained with a constraint.

11. The method of claim 10, wherein the at least one property of the plurality of concentric pipes is determined based on results of the first inversion.

12. The method of claim 10, further comprising displaying a result of the second inversion as a final inversion result.

13. The method of claim 10, wherein the constraint comprises a thickness of the concentric pipes identified to have nominal thickness from the first inversion.

14. The method of claim 10, wherein the constraint comprises a thickness of an innermost concentric pipe in addition to a thickness of the concentric pipes identified to have a nominal thickness from the first inversion.

15. The method of claim 10, wherein the constraint comprises a thickness of an innermost concentric pipe up to and including an innermost concentric pipe identified to have a thickness change from the first inversion.

16. The method of claim 10, wherein the at least one property of the plurality of concentric pipes of the second inversion comprises a magnetic permeability that is constrained to values computed in the first inversion.

17. The method of claim 10, wherein the constraint comprises results of the first inversion as an initial condition for the second inversion and an allowed thickness change within a fixed range only.

18. The method of claim 17, wherein the constraint further comprises a large weight to heavily penalize departure from an initial value.

19. A system comprising:
a corrosion detection tool, wherein the corrosion detection tool compromises a transmitter and a plurality of receivers; and
an information handling system operable to:
measure a signal to provide a measured response;
calibrate a log by matching a nominal value of the measured response to a synthetic response; and
run a first inversion, wherein the first inversion comprises a first subset of calibrated measurements that are used to compute a first estimate of properties of one or more pipes;
select an innermost concentric pipe from the one or more pipes for computing an impulse response for deconvolution for improving vertical resolution of the measured response;
apply deconvolution to a second subset of the calibrated measurements to provide calibrated and deconvolved measurements; and
run a second inversion on the second subset of calibrated and deconvolved measurements, wherein the second inversion comprises at least one property of the plurality of concentric pipes.

20. The system of claim 19, wherein the information handling system is further operable to identify the one or more pipes with an estimated thickness change from a nominal thickness to provide identified one or more pipes.

* * * * *